United States Patent [19]

Miller et al.

[11] Patent Number: 4,587,061

[45] Date of Patent: May 6, 1986

[54] OXIDATIVE RING CLEAVAGE PROCESS

[75] Inventors: William H. Miller, Glendale; Thomas E. Neumann, Creve Coeur, both of Mo.

[73] Assignee: Monsanto Company, St. Louis, Mo.

[21] Appl. No.: 741,931

[22] Filed: Jun. 6, 1985

[51] Int. Cl.$^4$ .............................................. C07F 9/38
[52] U.S. Cl. ...................... 260/502.5 F; 260/502.5 E
[58] Field of Search ................................. 260/502.5 F

[56] References Cited

U.S. PATENT DOCUMENTS 3,359,266 12/1967 Maier ................................. 260/246
4,047,927 9/1977 Gaertner et al. .............. 260/502.5 F
4,442,041 4/1984 Subramanian ................. 260/502.5 F

OTHER PUBLICATIONS

Fredericks et al., "Z. Naturforsch" 36C, 242–245 (1981).

Primary Examiner—J. E. Evans
Attorney, Agent, or Firm—David Bennett; Frank D. Shearin

[57] ABSTRACT

The novel reaction of 4-morpholinylmethylphosphonic acid with an aqueous alkali yields the trialkali metal salt of N-phosphonomethylglycine.

4 Claims, No Drawings

OXIDATIVE RING CLEAVAGE PROCESS

BACKGROUND TO THE INVENTION

This invention relates to a novel process for the production of N-phosphonomethylglycine, commonly called "glyphosate".

Glyphosate is the active ingredient in the commercial herbicide "Roundup" ® and is therefore a highly useful commodity. This invention describes a simple process for producing glyphosate from readily available materials.

DISCUSSION OF THE ART

Many processes have been described for the production of glyphosate including catalytic oxidation processes such as U.S. Pat. Nos. 3,969,398 and 4,147,719 in which a —$CH_2COOM$ group is removed from the glycine nitrogen of the glyphosate molecule (M is hydrogen or a salt-forming cation). This same reaction can also be accomplished electrolytically as described in U.S. Pat. No. 3,835,000.

Oxidative scission to produce a secondary amine from a tertiary amine has therefore been described in the context of the production of glyphosate but in each case a catalyst is required. This can be carbon, noble metal on carbon or a graphite electrode (in the case of the above electrolytic process).

In addition, in U.S. Pat. No. 4,442,041 it is shown that glyphosate can be produced by the reaction of $H_2O_3PCH_2N(CH_2CH_2OH)_2$ with sodium hydroxide in the presence of catalysts such as zinc oxide and cadmium oxide in an autoclave, followed by reaction with hydrochloric acid to generate glyphosate from its sodium salt. As will be appreciated, this reaction involves both the oxidation of an ethanolic group and the elimination of such a group from the molecule. This can be described as an oxidation/dealkylation reaction.

In the process of the invention the reaction is also, in a sense, an oxidation/dealkylation but it goes much further. In this process the reaction involves ring opening in a precise and controlled fashion that is nowhere taught in the prior art.

DESCRIPTION OF THE INVENTION

This invention provides a process for the production of N-phosphonomethylglycine (or "glyphosate") which comprises reacting 4-morpholinylmethylphosphonic acid with an amount of an aqueous alkali metal hydroxide in excess of that required to neutralize the acid in an autoclave at a temperature of from 200°–400° C. followed by acidification of the reaction product to liberate glyphosate.

The reaction mixture is alkaline and since the phosphonic acid derivative will initially react with the alkali to form the salt, the amount of alkali present must exceed that required to neutralize the acid. In practice then for each mole of the phosphonic acid derivative there must be more than two moles of alkali. Preferably the mole ratio of the phosphonic acid derivative to alkali should be from 1:3 to 1:15.

The alkali used can be the hydroxide of any alkali metal but practically speaking the alkali used is preferably sodium or potassium hydroxide.

The alkali metal hydroxide is conveniently used in concentrated aqueous solution, that is from about 30–50% by weight of the hydroxide. It is however possible, though less preferred, to use hydroxide concentrations outside of this range.

It should be realized of course that the above process is the functional equvalent of heating an ester or other hydrolyzable derivatives of the phosphonic acid compound under the same conditions. It is intended that this equivalent be embraced within the scope of this invention. Likewise the alkali metal salt of the acid can be prepared "in situ" as described above, or it can be preformed by reaction of the acid with the appropriate alkali metal hydroxide.

The reaction temperature employed is from 200° to 400° C. and within this range temperatures of from 250° to 350° C. are generally most preferred.

Such elevated temperatures clearly will lead to loss of solvent or associated water. It is preferred that the reaction occurs in a closed vessel and thus the reaction usually involves operation under autogenous pressure.

The starting material for the process of the invention, 4-morpholinylmethylphosphonic acid, is readily prepared by the reaction of morpholine with chloromethylphosphonic acid as described by Fredericks and Summers in "Synthesis and Biological Activity of Aminomethylphosphonic Acids Related to the Herbicide Glyphosate" (Z. Naturforsch. 36c. pp 242-5, 1981).

Alternatively, the starting material can be prepared by the reaction of morpholine with formaldehyde and phosphorous acid as described in U.S. Pat. No. 3288846 (Moedritzer and Irani).

The major by-product of this invention, aminomethylphosphonic acid, may be converted in situ to glyphosate using the method described in U.S. application Ser. No. 687,305 filed 12/28/84, thus facilitating the workup and increasing the overall yield at the desired product.

DESCRIPTION OF SPECIFIC EMBODIMENTS

The process of the invention is further illustrated by the following Examples which are for the purposes of illustration only and are not to be taken as implying any necessary limitation on the essential scope of the invention.

EXAMPLE 1

In a 100 mL Monel autoclave were mixed 1.99 g (11.0 mmol) of 4-morpholinylmethylphosphonic acid and 13.1 g (165 mmol) of a 50.3% solution of NaOH to give a slurry. The reaction vessel was sealed and heated to 250° C. for two hours. There was only a small increase in internal pressure during the heating period. The temperature of the reaction was then raised to 300° C. for three hours. In the span of this heating period the internal pressure rose from $2.4 \times 10^6$ $N/M^2$ to $4.0 \times 10^6$ $N/M^2$. The reaction was cooled to room temperature and the residual internal pressure was vented off. The reaction mixture, which consisted of a white slurry, was diluted with 10 mL of water and neutralized by the addition of 13.6 mL of conc. HCl. The resulting solution was concentrated to dryness. The residue was taken up in conc. HCl and the precipitated NaCl was filtered away. The final filtrate was concentrated and purified by ion exchange chromatography (Dowex 50X8-400) to yield 0.82 g (44.1%) of N-phosphonomethylglycine (NMR, $D_2O$) δ 4.07 (s, 2H), 3.25 (d, J=12 Hz, 2H) and 0.40 g (32.8%) of aminomethylphosphonic acid (NMR, $D_2O$) δ 3.06 (d, J=12 Hz, 2H) based on the amount of starting substrate.

EXAMPLE 2

In a 100 mL Monel autoclave were mixed 4.0 g (22 mmol) of 4-morpholinylmethylphosphonic acid and 26.3 g (330 mmol) of a 50.3% solution of NaOH. The vessel was sealed and heated to 275° C. for four hours. The reaction was cooled to room temperature and the residual pressure generated by the reaction was vented off. The reaction mixture was a white slurry which was diluted with 10 mL of $H_2O$ and neutralized with 27.2 mL (330 mmol) of conc. HCl. This solution was concentrated to dryness. The residue was taken up in conc. HCl and the precipitated NaCl was filtered off. The filtrate was concentrated and purified by ion exchange chromatography to yield 1.29 g (34.7%) of N-phosphonomethylglycine, 0.57 g (23%) of aminomethylphosphonic acid, 0.67 g (19.6%) of N-(2-hydroxyethyl)aminomethylphosphonic acid, and 0.46 g (11.6%) of unreacted starting material.

EXAMPLE 3

To a 100 mL Monel autoclave were added 2.23 g (12.3 mmol) of 4-morpholinylmethylphosphonic acid 7.88 g (98.5 mmol) of a 50% solution of NaOH, and 10 mL of $H_2O$ to give a slurry. The vessel was flushed with $N_2$, sealed and heated to 250° C. This temperature was maintained for five and one-half hours with little noticeable reaction occurring. The temperature was then raised to 300° C. for three hours. During this period the internal pressure in the vessel rose from $4.5 \times 10^6$ $N/M^2$ to $5.7 \times 10^6$ $N/M^2$. The vessel was cooled to room temperature and the residual pressure was released. The resulting solution was diluted with water and neutralized with 8.1 mL (98.5 mmol) of conc. HCl. The solution was concentrated to dryness. The residue was taken up in conc. HCl and the precipitated NaCl was filtered away. The final filtrate was concentrated and purified by ion exchange chromatography to yield 0.71 g (34.1%) of N-phosphonomethylglycine and 0.43 g (31.5%) of aminomethylphosphonic acid.

What is claimed is:

1. A process for the production of N-phosphonomethylglycine which comprises reacting 4-morpholinylmethylphosphonic acid with an amount of an aqueous alkali metal hydroxide in excess of that required to neutralize the acid in an autoclave at a temperature of 200°–400° C. followed by acid neutralization of the reaction product to liberate N-phosphonomethylglycine.

2. A process according to claim 1 in which a 3:1 to 15:1 molar excess of alkali metal hydroxide is used.

3. A process according to claim 1 in which the alkali metal hydroxide is sodium hydroxide.

4. A process according to claim 1 in which the reaction is carried out at 250° to 350° C.

* * * * *